United States Patent [19]
Szostak et al.

[11] Patent Number: 5,910,408
[45] Date of Patent: Jun. 8, 1999

[54] CATALYTIC DNA HAVING LIGASE ACTIVITY

[75] Inventors: Jack W. Szostak, Boston, Mass.; Bernard Cuenoud, Basel, Switzerland; David E. Huizenga, Winthrop, Mass.

[73] Assignee: The General Hospital Corporation, Boston, Mass.

[21] Appl. No.: 08/487,867

[22] Filed: Jun. 7, 1995

[51] Int. Cl.⁶ .............................. C12Q 1/68; C12P 19/34; C07H 21/04

[52] U.S. Cl. .............................. 435/6; 435/15; 435/91.2; 435/183; 536/23.1; 536/25.4

[58] Field of Search .............................. 435/6, 91.2, 183, 435/15, 18, 19; 536/23.1, 25.4

[56] References Cited

U.S. PATENT DOCUMENTS

| | | | |
|---|---|---|---|
| 5,037,746 | 8/1991 | Cech et al. | 435/91 |
| 5,116,742 | 5/1992 | Cech et al. | 435/91 |
| 5,180,818 | 1/1993 | Cech et al. | 536/23.1 |
| 5,270,163 | 12/1993 | Gold et al. | 435/6 |
| 5,334,711 | 8/1994 | Sproat et al. | 536/24.5 |

OTHER PUBLICATIONS

Bartel and Szostak, Isolation of New Ribozymes from a Large Pool of Random Sequences, Science 261:1411–1418, 1993.
Bartel et al., HIV–1 Rev Regulation Involves Recognition of Non–Watson–Crick Base Pairs in Viral RNA, Cell 67:529–536, 1991.
Beaudry and Joyce, Directed Evolution of an RNA Enzyme, Science 257:635–641, 1992.
Been and Perrotta, Group I Intron Self–Splicing with Adenosine: Evidence for a Single Nucleoside–Binding Site, Science 252:434–437, 1990.
Benner et al., Modern Metabolism as a Palimpsest of the RNA World, Proc. Natl. Acad. Sci. USA 86:7054–7058, 1989.
Blackburn, Telomerases, Ann. Rev. Biochem. 61:113–129, 1992.
Bock et al., Selection of Single–Stranded DNA Molecules that bind and Inhibit Human Thrombin, Nature 355:564–566, 1992.
Bratty et al., The Hammerhead RNA Domain, a Model Ribozyme, Biochimica et Biophysica Acta 1216:345–59, 1993.
Breaker and Joyce, A DNA Enzyme that Cleaves RNA, Chemistry & Biology 1:223–229, 1994.
Breaker and Joyce, Inventing and Improving Ribozyme Function: Rational Design Versus Iterative Selection Methods, Trends in Biotechnology—TIBTECH 12:268–275, 1994.
Chartrand et al., An Oligodeoxyribonucleotide with Catalytic Properties, RNA Processing 77 (Proceedings of the RNA Society, Madison, Wisconsin, 1994).
Chu et al., Synthesis of an Amplifiable Reporter RNA for Bioassays, Nucleic Acids Research 14:5591–5606, 1986.
Connell et al., Three Small Ribooligonucleotides with Specific Arginine Sites, Biochemistry 32:5497–5502, 1993.
Dahm et al., Evidence for the Role of Solvated Metal Hydroxide in the Hammerhead Cleavage Mechanism, Biochemistry 32:13040–13045, 1993.
Dolinnaya et al., The Use of BrCN for Assembling Modified DNA Duplexes and DNA–RNA Hybrids; Comparison with Water–Soluble Carbodiimide, Nucleic Acids Research 19:3067–3072, 1991.
Dolinnaya et al., Site–directed Modification of DNA Duplexes by Chemical Ligation, Nucleic Acids Research 16:3721–3738, 1988.

(List continued on next page.)

*Primary Examiner*—Kenneth R. Horlick
*Attorney, Agent, or Firm*—Clark & Elbing LLP

[57] ABSTRACT

The invention features nucleic acid molecules and, in particular, DNA molecules having catalytic activity, as well as methods for obtaining and using such nucleic acid molecules.

17 Claims, 8 Drawing Sheets

OTHER PUBLICATIONS

Ellington and Szostak, Selection in vitro of Single–stranded DNA Molecules that Fold into Specific Ligand–binding Structures, Nature 355:850–852, 1992.

Ellington and Szostak, In vitro Selection of RNA Molecules that Bind Specific Ligands, Nature 346:818–822, 1990.

Famulok, Molecular Recognition of Amino Acids by RNA–Aptamers: An L–Citrulline Binding RNA Motif and Its Evolution into an L–Arginine Binder, J. Am. Chem. Soc. 116:1698–1706, 1994.

Famulok and Szostak, Stereospecific Recognition of Tryptophan Agarose by in Vitro Selected RNA, J. Am. Chem. Soc. 114:3990–3991, 1992.

Green and Szostak, Selection of a Ribozyme that Functions as a Superior Template in a Self–Copying Reaction, Science 258:1910–1915, 1992.

Haseloff and Gerlach, Simple RNA Enzymes with New and Highly Specific Endoribonuclease Activities, Nature 334:585–591, 1988.

Huizenga and Szostak, A DNA Aptamer that Binds Adenosine and ATP, Biochemistry 34:656–665, 1995.

Inoue and Orgel, A Nonenzymatic RNA Polymerase Model, Science 219:859–862, 1983.

Inoue and Orgel, Oligomerization of (Guanosine 5'–phosphor)–2–methylimidazolide on Poly(C)–An RNA Polymerase Model, J. Mol. Biol. 162:201–217, 1982.

Jenison et al., High–Resolution Molecular Discrimination by RNA, Science 263:1425–1429, 1994.

Joyce, RNA Evolution and the Origins of Life, Nature 338:217–223, 1989.

Joyce et al., Non–enzymatic Template–directed Synthesis on RNA Random Copolymers–Poly(C, U) Templates, J. Mol. Biol. 176:279–306, 1984.

Kao and Crothers, A Proton–coupled Conformational Switch of *Escherichia coli* 5S Ribosomal RNA, Proc. Natl. Acad. Sci. USA 77:3360–3364, 1980.

Karlin, Metalloenzymes, Structural Motifs, and Inorganic Models, Science 261:701–708, 1993.

Khan and Roe, Aminoacylation of Synthetic DNAs Corresponding to *Escherichia coli* Phenylalanine and Lysine tRNAs, Science 241:74–76, 1988.

Lehman & Joyce, Evolution in vitro of an RNA Enzyme with Altered Metal Dependence, Nature 361:182–185. 1993.

Lerner et al., At the Crossroads of Chemistry and Immunology: Catalytic Antibodies, Science 252:659–67, 1991.

Lorsch and Szostak, In vitro Selection of RNA Aptamers Specific for Cyanocobalamin, Biochemistry 33:973–982, 1994.

Luebke and Dervan, Nonenzymatic Ligation of Oligodeoxyribonucleotides on a Duplex DNA Template by Triple–Helix Formation, J. Am. Chem. Soc. 111:8733–8735, 1989.

Naylor and Gilham, Studies on Some Interactions and Reactions of Oligonucleotides in Aqueous Solution, Biochemistry 5:2722–2728, 1966.

Orgel, The Origin of Life on the Earth–Growing Evidence Supports the Idea that the Emergence of Catalytic RNA was a Crucial Early Step. How that RNA Came into Being Remains Unknown, Scientific Am., pp. 77–83, Oct. 1994.

Orgel, Molecular Replication, Nature 358:203–209, 1992.

Paborsky et al., The Single–stranded DNA Aptamer–binding Site of Human Thrombin, J. Biol. Chem. 268:20808–20811, 1993.

Padmanabhan et al., The Structure of α–Thrombin Inhibited by a 15–Mer Single–stranded DNA Aptamer, J. Biol. Chem. 268:17651–17654, 1993.

Pan and Uhlenbeck, In Vitro Selection of RNAs that Undergo Autolytic Cleavage with $Pb^{2+}$, Biochemistry 31:3887–3895, 1992.

Pan et al., Properties of an In Vitro Selected $Pb^{2+}$ Cleavage Motif, Biochemistry 33:9561–9565, 1994.

Perreault et al., The Synthesis and Functional Evaluation of RNA and DNA Polymers having the Sequence of *Escherichia coli* $tRNA^{fMet}$, Eur. J. Biochem. 186:87–93, 1989.

Pyle, Ribozymes: A Distinct Class of Metalloenzymes, Science 261:709–714, 1993.

Sassanfar and Szostak, An RNA Motif that Binds ATP, Nature 364:550–553, 1993.

Shabarova et al., DNA–like Duplexes with Repetitions. III. Efficient Template–guided Chemical Polymerization of d(TGGCCAAGCTp), Nucleic Acids Research 9:5747–5761, 1981.

Szostak, In Vitro Genetics, Trends in Biochemical Sciences 17:89–93, 1992.

Tsai et al., In Vitro Selection of an RNA Epitope Immunologically Cross–Reactive with a Peptide, Proc. Natl. Acad. Sci. USA 89:8864–8868, 1992.

Tuerk and Gold, Systematic Evolution of Ligands by Exponential Enrichment: RNA Ligands to Bacteriophage T4 DNA Polymerase, Science 249:505–510, 1990.

Uhlenbeck, A Small Catalytic Oligoribonucleotide, Nature 328:596–600, 1987.

Wang et al., The Tertiary Structure of a DNA Aptamer which Binds to and Inhibits Thrombin Determines Activity, Biochemistry 32:11285–11292, 1993.

Wilson and Szostak, Ribozyme Catalysis, Current Opinion in Structural Biology 2:749–756, 1992.

Wu and Orgel, Nonenzymatic Template–Directed Synthesis on Hairpin Oligonucleotides. 2. Templates Containing Cytidine and Guanosine Residues, J. Am. Chem. Soc. 114:5496–5501, 1992.

Wyatt et al., Combinatorially Selected Guanosine–quartet Structure is a Potent Inhibitor of Human Immunodeficiency Virus Envelope–mediated Cell Fusion, Proc. Natl. Acad. Sci. USA 91:1356–1360, 1994.

Schwartz et al., Template–Directed Synthesis of Novel, Nucleic Acid–Like Structures, Science 228:585–87, 1985.

Yang et al., *Biochemistry* 31, 5005–5009 (1992).

Cuenoud et al., *Nature* 375, 611–614 (1995).

Chartrand et al., *Nucleic Acids Res.* 23(20), 4092–4096(1995).

Ekland et al., *Science* 269, 364–370 (1995).

Burgstaller et al., *Angew. Chem. Int. Ed. Engl.* 34(11), 1189–1192(1995).

```
         1         10        20        30        40        50        60
         |         |         |         |         |         |         |
Seq01    TATGTGTCGATTGTGTTCTTTCGCTAGACCATGTGAGACTTATGCTTCGAATTGTCGAGT
Seq02    TATGTGTCGATTGTGTTCTTTCGCTAGACCATGTGGGACTTATGCTTCGAATTGTCGAGT
Seq03    TATGTGTCGATTGTGTTCTTTCGCTAGACCATGTGAGACTTATGCTTCGAATTGTCGAGT
Seq04    TATGTGTCGATTGTGTTCTTCCGCTAGACCATGTGAGACTTATGCTTCGAATTGTCGAGT
Seq05    TATAGTCAGGCTGGTAGGGTTCTTTCGCAGAGTGCGATGTGTTTTGATTTGAACTTATTT
Seq06    TATAGTCAGGCTGGTAGGGTTCTTTCGCAGAGTGCGATGTGTTTTGATTTGAACTTATTT
Seq07    TATAGTCAGGCTGGTAGGGTTCTTTCGCAGAGTGCGATGTGTTTTGATTTGAACTTATTT
Seq08    TATAGTCAGGCTGGTAGGGTTCTTTCGCAGAGTGCGATGTGTTTTGATTTGAACTTATTT
Seq09    CGTTTCGTTTTGGAAGGCCTGTTGGTCCTTGTGTTCTCTCGCAGACCACTTTTTCGTACA
Seq10    CGTTTCGATTTGGAAGGCCTGTTGGTCCTTGTGTTCTCTCGCAGACCACTTTTTCGTTCA
Seq11    CGTTTCGTTTTGGAAGGCCTGTTGGTCCTTGTGTTCTCTCGCAGACCACTTTTTCGTTCA
Seq12    CGTCTTGCTGGGTTTTTGCTCGGTATCGTTCTTTCGCTAGACCTTTAAATAATGGTGAGA
Seq13    CACGTACTTCTTGTAGACGTGTGGCTTTGATAGGATGTGGTCTTTCGCTAGAGTTAATTA
Seq14    GAGCGTGGCTAACTGGATAGTGGTCTCTCGCTAGACACCTGTGTGAGATTGTTAGAATGC
Seq15    GTTTTTGTGTTTGACGAATACGTGTTCTTTCGCAGACCTTGTGCATCTTTGTTGTCGAA
Seq16    TTGTGGTTGTGACCGGTTAGGATAGTGTTATTTCGCAGACCACATCACCGTATTTTGGTG
Seq17    TTTGGTTTCGCAGTTGGTGTGTTCGTTCGCAGACCCTTTGGGTGAGATTGCTTTTGCGGC
Seq18    TGGGGATCGCGGTATTAGTGTGTGCGTACTTTGGCTGACGGTGGCCGTCGTGGTATGTCT
Seq19    TTTCTTGGGCTTAAGCTCGGTTATTGTTCTTTCGCTAGATCCATGTCTATATTATGGTTG
Seq20    TCAGGTGTTTTTGTTTTTCTGAGCAGGGAGTCGGTGTGTTCTTTCGCAGACACGAGTTTT
Seq21    GTCGGTTCATGTTGTTCTTTCGCCAGATCATCGGGGCGTTTTAGTTTACGTCACTCGACG 70        80        90        100       110
                   |         |         |         |         |
         TTTTGACTGTTTGCTTGGCCGGCTGGTGGTCGTGCATGGTGAGATGATTACCCTA
         TTTTGACTGTTTGCTTGGCTGGCTGGTGGCCGCGCATGGTGAGATGATTATCCCT
         TTTTGACTGTTTGCTTGGCCGGCTGGTGGTCGCGCATGGTGAGATGATTATCCCTA
         TTTTGACTGTTTGCTTGGCCGGCTGGTGGTCGCGCATGGTGAGATGATTATTCCCTG
         ATGAGGTCTGTTGAAGCCCATTGCGACTGAGTGCTTGCTGCTTGTTACTTTCCCTT
         ATGAGGTCTGTTGAAGCCCATTGCGACTGAGTGCTTGCTGCTTGTTACTTTCCCAT
         ATGAGGTCTGTTGAAGCCCATTGCGACTGAGTGCTTGCGGCTTGTTACTTTCCCAT
         ATGAGGTCGGTTGAAGCTCATTGCGACTGAGTGCTTGCTGCTTGTTACTTTCCCAC
         CGGAAGTGGATTAAGTGGTGAGTTGCTTTCTAGTATGCGCTTTGAGGTATTCTATG
         CGGAAGTGGAATAAGTGGTGAGTTGCTTTCTAGTGTGCGCTTTGAGGTATTCTATG
         CGGAAGTGGATTAAGTGGTGAGTTGCTTTCTAGTGTGCGCTTTGAGGAATTCTATG
         TGCTGTTTTTGAGGCTAGTAGCGCGGGATTGGGCGTTACCGTCGTTTGTCTTTCGA
         GCTGTGGACCCTTAAGGTGTCTTAACTGAGATGCTTTCATTTTGTCTTTCTGATT
         GGTCCATCTGCCTATTTGGTAGTTAAGGGTTTATGCTGTTCCTCTGATCACTTTCG
         GGTGAGATGCTTGTGTTGTTTGCTTTTTCATGTTTGCTTGTCCTTGTTTTTAAAC
         AGTGGTGAGATGCTGCTATTTTGTGGTGTTGCACCCGCTTAAATACTTCGAGGTTT
         TTTGAGTGATCCTGCCTTGTGGTATTGTTGTGCATGTGATAGCTTGTTCTGCTCAT
         GTTCTGTCGCATGATCCAATCTTCCCGGTTGGATGAGATGCTTGATTATGCTTA
         GGCCGACTGGTTTTTTACTTATACTATTGTTTTTGTGGCGTGGATGAGATGCTGTTT
         TTGTGTGAGATTGCTTAGTGTTCTTTGTTCAATCACTAGATTTCTTGATGGGTGTG
         TATTTTCTACGGGGTTTAGGCTTTGTCGATCATGAGTTGCTTAGATTGATTTTTT
```

FIG. 2B

| | $k_{obs}$ hr$^{-1}$ |
|---|---|
| E47 | 3.4 |
| E47-3T | <0.01 |
| E47-AGA | <0.01 |
| E47-hairpin | 0.41 |
| Pool 9 | 1.7 |
| templated bkgrd. | 0.0011 |
| background | <2x10$^{-5}$ |

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
    (A) LENGTH: 115 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:1:

TATGTGTCGA TTGTGTTCTT TCGCTAGACC ATGTGAGACT TATGCTTCGA ATTGTCGAGT        60

TTTTGACTGT TTGCTTGGCC GGCTGGTGGT CGTGCATGGT GAGATGATTA CCCTA           115

(2) INFORMATION FOR SEQ ID NO:2:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

TATGTGTCGA TTGTGTTCTT TCGCTAGACC ATGTGGGACT TATGCTTCGA ATTGTCGAGT        60

TTTTGACTGT TTGCTTGGCT GGCTGGTGGC CGCGCATGGT GAGATGATTA TCCCT           115

(2) INFORMATION FOR SEQ ID NO:3:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

TATGTGTCGA TTGTGTTCTT TCGCTAGACC ATGTGAGACT TATGCTTCGA ATTGTCGAGT        60

TTTTGACTGT TTGCTTGGCC GGCTGGTGGT CGCGCATGGT GAGATGATTA TCCCTA          116

(2) INFORMATION FOR SEQ ID NO:4:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TATGTGTCGA TTGTGTTCTT CCGCTAGACC ATGTGAGACT TATGCTTCGA ATTGTCGAGT        60

TTTTGACTGT TTGCTTGGCC GGCTGGTGGT CGCGCATGGT GAGATGATTA TTCCCTG         117

(2) INFORMATION FOR SEQ ID NO:5:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

TATAGTCAGG CTGGTAGGGT TCTTTCGCAG AGTGCGATGT GTTTTGATTT GAACTTATTT        60

```
ATGAGGTCTG TTGAAGCCCA TTGCGACTGA GTGCTTGCTG CTTGTTACTT TCCCTT      116
```

(2) INFORMATION FOR SEQ ID NO:6:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
TATAGTCAGG CTGGTAGGGT TCTTTCGCAG AGTGCGATGT GTTTTGATTT GAACTTATTT   60
ATGAGGTCTG TTGAAGCCCA TTGCGACTGA GTGCTTGCTG CTTGTTACTT TCCCAT      116
```

(2) INFORMATION FOR SEQ ID NO:7:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
TATAGTCAGG CTGGTAGGGT TCTTTCGCAG AGTGCGATGT GTTTTGATTT GAACTTATTT   60
ATGAGGTCTG TTGAAGCCCA TTGCGACTGA GTGCTTGCGG CTTGTTACTT TCCCAT      116
```

(2) INFORMATION FOR SEQ ID NO:8:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
TATAGTCAGG CTGGTAGGGT TCTTTCGCAG AGTGCGATGT GTTTTGATTT GAACTTATTT   60
ATGAGGTCGG TTGAAGCTCA TTGCGACTGA GTGCTTGCTG CTTGTTACTT TCCCAC      116
```

(2) INFORMATION FOR SEQ ID NO:9:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
CGTTTCGTTT TGGAAGGCCT GTTGGTCCTT GTGTTCTCTC GCAGACCACT TTTTCGTACA   60
CGGAAGTGGA TTAAGTGGTG AGTTGCTTTC TAGTATGCGC TTTGAGGTAT TCTATG      116
```

(2) INFORMATION FOR SEQ ID NO:10:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CGTTTCGATT TGGAAGGCCT GTTGGTCCTT GTGTTCTCTC GCAGACCACT TTTTCGTTCA        60

CGGAAGTGGA ATAAGTGGTG AGTTGCTTTC TAGTGTGCGC TTTGAGGTAT TCTATG        116

(2) INFORMATION FOR SEQ ID NO:11:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CGTTTCGTTT TGGAAGGCCT GTTGGTCCTT GTGTTCTCTC GCAGACCACT TTTTCGTTCA        60

CGGAAGTGGA TTAAGTGGTG AGTTGCTTTC TAGTGTGCGC TTTGAGGAAT TCTATG        116

(2) INFORMATION FOR SEQ ID NO:12:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

CGTCTTGCTG GGTTTTTGCT CGGTATCGTT CTTTCGCTAG ACCTTTAAAT AATGGTGAGA        60

TGCTGTTTTT GAGGCTAGTA GCGCGGGATT GGGCGTTACC GTCGTTTGTC TTTCGA        116

(2) INFORMATION FOR SEQ ID NO:13:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

CACGTACTTC TTGTAGACGT GTGGCTTTGA TAGGATGTGG TCTTTCGCTA GAGTTAATTA        60

GCTGTGGACC CTTAAGGTGT CTTAACTGAG ATGCTTTCAT TTTGTCTTTC TGATT        115

(2) INFORMATION FOR SEQ ID NO:14:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GAGCGTGGCT AACTGGATAG TGGTCTCTCG CTAGACACCT GTGTGAGATT GTTAGAATGC        60

GGTCCATCTG CCTATTTGGT AGTTAAGGGT TTATGCTGTT CCTCTGATCA CTTTCG        116

(2) INFORMATION FOR SEQ ID NO:15:

(i) SEQUENCE CHARACTERISTICS:
        (A) LENGTH: 115 base pairs (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:15:

GTTTTTGTGT TTGACGAATA CGTGTTCTTT CGCAGACCTT GTGCATCTTT GTTGTCGCAA        60

GGTGAGATGC TTGTGTTGTT TGCTTTTTCA TGTTTGCTTG TCCTTGTTTT TAAAC            115

(2) INFORMATION FOR SEQ ID NO:16:

(i) SEQUENCE CHARACTERISTICS:
            (A) LENGTH: 116 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:16:

TTGTGGTTGT GACCGGTTAG GATAGTGTTA TTTCGCAGAC CACATCACCG TATTTTGGTG        60

AGTGGTGAGA TGCTGCTATT TTGTGGTGTT GCACCCGCTT AAATACTTCG AGGTTT           116

(2) INFORMATION FOR SEQ ID NO:17:

(i) SEQUENCE CHARACTERISTICS:
            (A) LENGTH: 116 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:17:

TTTGGTTTCG CAGTTGGTGT GTTCGTTCGC AGACCCTTTG GGTGAGATTG CTTTTGCGGC        60

TTTGAGTGAT CCTGCCTTGT GGTATTGTTG TGCATGTGAT AGCTTGTTCT GCTCAT           116

(2) INFORMATION FOR SEQ ID NO:18:

(i) SEQUENCE CHARACTERISTICS:
            (A) LENGTH: 114 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:18:

TGGGGATCGC GGTATTAGTG TGTGCGTACT TTGGCTGACG GTGGCCGTCG TGGTATGTCT        60

GTTCTGTCGC ATGATCCAAT CTTCCCGGTT GGATGAGATG CTTGATTATG CTTA             114

(2) INFORMATION FOR SEQ ID NO:19:

(i) SEQUENCE CHARACTERISTICS:
            (A) LENGTH: 117 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:19:

TTTCTTGGGC TTAAGCTCGG TTATTGTTCT TTCGCTAGAT CCATGTCTAT ATTATGGTTG        60

GGCCGACTGG TTTTTTACTT ATACTATTGT TTTTGTGGCG TGGATGAGAT GCTGTTT          117

(2) INFORMATION FOR SEQ ID NO:20:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

```
TCAGGTGTTT TTGTTTTTCT GAGCAGGGAG TCGGTGTGTT CTTTCGCAGA CACGAGTTTT      60

TTGTGTGAGA TTGCTTAGTG TTCTTTGTTC AATCACTAGA TTTCTTGATG GGTGTG         116
```

(2) INFORMATION FOR SEQ ID NO:21:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

```
GTCGGTTCAT GTTGTTCTTT CGCCAGATGA TCGCGGCGTT TTAGTTTACG TCACTCGACG      60

TATTTTCTAC GGGGTTTAGG CTTTGTCGAT CATGAGTTGC TTAGATTGAT TTTTT          115
```

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

```
CGGATAGTGT TCTTTCGCTA GANNNNN                                          27
```

(2) INFORMATION FOR SEQ ID NO:23:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

```
NNNNNTGAGA TGCTT                                                       15
```

(2) INFORMATION FOR SEQ ID NO:24:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

```
AAGCATCTCA AGC                                                         13
```

(2) INFORMATION FOR SEQ ID NO:25:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

GGAACACTAT CCG                                              13

(2) INFORMATION FOR SEQ ID NO:26:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

CGGATAGTGT TCTTTCGCTA GANNNN                            26

(2) INFORMATION FOR SEQ ID NO:27:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

NNNNTGAGAT GCTT                                            14

(2) INFORMATION FOR SEQ ID NO:28:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

CGGATAGTGT TCTTTCGCTA GACCATGTGA CGCATGGTGA GATGCTT           47

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

GGAACACTAT CCGACTGGCA CC                                  22

(2) INFORMATION FOR SEQ ID NO:30:

(i) SEQUENCE CHARACTERISTICS:
        (A) LENGTH: 20 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:30:

CGGGATCCTA ATGACCAAGG                                                         20

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

AAGCATCTAA GCATCTCAAG C                                                       21

(2) INFORMATION FOR SEQ ID NO:32:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

CGGATAGTGT TCCGCTTGAG ATGCTT                                                  26

(2) INFORMATION FOR SEQ ID NO:33:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

ACCTTCACCT TCTTTCGCTA GACCTTCAAG CGGAAGGTGA AGGTCTAGCG                        50

(2) INFORMATION FOR SEQ ID NO:34:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

ACCTTCACCT TCTTTCGCTA GACCTTCAAG C                                            31

(2) INFORMATION FOR SEQ ID NO:35:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

GGAAGGTGAA GGTCTAGCG                                        19

(2) INFORMATION FOR SEQ ID NO:36:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

ACCTTCACCT TCTTTCGCTA GACCTTCAAG CGGAAGGTGA AGGTCTA         47

(2) INFORMATION FOR SEQ ID NO:37:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

GGAAGGTGAA GGTCTA                                           16

(2) INFORMATION FOR SEQ ID NO:38:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

CTTCACCTTC TTTCGCTAGA CCTTCAAGCG GAAGGTGAAG GTCTA           45

(2) INFORMATION FOR SEQ ID NO:39:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

CTTCACCTTC TTTCGCTAGA CCTTCAAGC                             29

CATALYTIC DNA HAVING LIGASE ACTIVITY

This invention was made with Government support under Contract #GM-45315 awarded by the National Institutes of Health. The government has certain rights in the invention.

BACKGROUND OF THE INVENTION

This invention relates to DNA molecules having catalytic activity and methods of obtaining and using such DNA molecules.

Ribozymes are highly structured RNA molecules that carry out specific chemical reactions (e.g., cleavage of RNA, cleavage of DNA, polymerization of RNA, and replication of RNA), often with kinetic efficiencies comparable to those of most engineered enzymes.

SUMMARY OF THE INVENTION

The invention features nucleic acid molecules having catalytic activity, as well as methods for obtaining and using such nucleic acid molecules.

The methods of the invention entail sequential in vitro selection and isolation of nucleic acid molecules having the desired properties (e.g., catalytic activity, such as ligase activity) from pools of single-stranded nucleic acid molecules (e.g., DNA, RNA, or modifications or combinations thereof) containing random sequences. The isolated nucleic acid molecules are then amplified by using, e.g., the polymerase chain reaction (PCR).

The rounds of selection and amplification may be repeated one or more times, after each round, the pool of molecules being enriched for those molecules having the desired activity. Although the number of desired molecules in the initial pool may be exceedingly small, the sequential selection scheme overcomes this problem by repeatedly enriching for the desired molecules.

The pool of single-stranded nucleic acid molecules employed in the invention may be referred to as "random nucleic acid molecules" or as containing "random sequences." These general terms are used to describe molecules or sequences which have one or more regions of "fully random sequence." In a fully random sequence, there is an approximately equal probability of A, T/U, C, or G being present at each position in the sequence. Of course, the limitations of some methods used to create nucleic acid molecules make it rather difficult to synthesize fully random sequences in which the probability of each nucleotide occurring at each position is absolutely equal. Accordingly, sequences in which the probabilities are roughly equal are considered fully random sequences.

In "partially random sequences" and "partially randomized sequences," rather than there being a 25% chance of A, T/U, C, or G being present at each position, there are unequal probabilities. For example, in a partially random sequence, there may be a 70% chance of A being present at a given position and a 10% chance of each of T/U, C, or G being present at that position. Further, the probabilities can be the same or different at each position within the partially randomized region. Thus, a partially random sequence may include one or more positions at which the sequence is fully random, one or more positions at which the sequence is partially random, and/or one or more positions at which the sequence is defined.

Partially random sequences are particularly useful when one wishes to make variants of a known sequence. For example, if one knows that a particular 50 nucleotide sequence possesses a desired catalytic activity and that positions 5, 7, 8, and 9 are critical for this activity, one could prepare a partially random version of the 50 nucleotide sequence in which the bases at positions 5, 7, 8, and 9 are the same as in the catalytically active sequence, and the other positions are fully randomized. Alternatively, one could prepare a partially random sequence in which positions 5, 7, 8, and 9 are partially randomized, but with a strong bias towards the bases found at each position in the original molecule, with all of the other positions being fully randomized. This type of partially random sequence is desirable in pools of molecules from which catalytic nucleic acids are being selected. The sequence of any randomized region may be further randomized by mutagenesis during one or more amplification steps.

In addition to random or partially random sequences, it may also be desirable to have one or more regions of "defined sequence." A defined sequence is a sequence selected or known by the creator of the molecule. Defined sequence regions are useful for isolating or PCR amplifying the nucleic acid molecule because they may be recognized by defined complementary primers. The defined sequence regions may flank the random regions or be intermingled with the random regions. The defined regions can be of any length desired and are readily designed using knowledge in the art (see, for example, Ausubel et al., *Current Protocols in Molecular Biology,* Greene Publishing, New York, N.Y. (1994); Ehrlich, *PCR Technology,* Stockton Press, New York, N.Y. (1989); and Innis et al., *PCR Protocols, A Guide to Methods and Applications,* Academic Press, Inc., San Diego, Calif. (1990)).

The selection method of the invention involves contacting a pool of nucleic acid molecules containing random sequences with the substrate for the desired catalytic activity under conditions (including, e.g., nucleic acid molecule concentrations, temperature, pH, and salt) which are favorable for the catalytic activity. Nucleic acid molecules having the catalytic activity are partitioned from those which do not, and the partitioned nucleic acid molecules having the catalytic activity then are amplified using, e.g., PCR.

The steps of contacting, partitioning, and amplifying may be repeated any desired number of times. Several cycles of selection (contacting, partitioning, and amplifying) may be desirable because after each round the pool is more enriched for the desired catalytic nucleic acids. One may choose to perform so many cycles of selection that no substantial improvement in catalytic activity is observed upon further selection, or one may carry out far fewer cycles of selection.

Methods known in the art may be used at particular steps of this selection and isolation procedure, and one skilled in the art is referred to Ellington and Szostak, Nature 346:818–822, 1990; Lorsch and Szostak, Nature 371:31–36, 1994; Tuerk and Gold, Science 249:505–510, 1990; and methods described herein.

In addition, one may mutagenize isolated catalytic nucleic acids in order to generate and subsequently isolate molecules exhibiting improved catalytic activity. For example, one may prepare degenerate pools of single-stranded nucleic acids based on a particular catalytic nucleic acid sequence, or one may first identify important regions in a catalytic nucleic acid sequence (for example, by standard deletion analysis), and then prepare pools of candidate catalytic nucleic acid molecules that include degenerate sequences at those important regions.

Those skilled in the art can readily identify catalytic nucleic acid consensus sequences by sequencing a number of catalytic nucleic acid molecules and comparing their sequences. In some cases, such sequencing and comparison will reveal the presence of a number of different conserved sequences. In these circumstances, one may identify a core sequence which is common to most or all of the isolated sequences. This core sequence, or variants thereof, may be used as the starting point for the selection of improved catalysts. By "variant" of a sequence is meant a sequence created by partially randomizing the sequence.

The size of the randomized regions employed should be adequate to provide a catalytic site. Thus, the randomized region used in the initial selection preferably includes between 10 and 300 nucleotides, for example, between 25 and 180 nucleotides.

It may be desirable to increase the stringency of a selection step in order to isolate more molecules. The stringency of the selection step may be increased by decreasing substrate concentration. The stringency of the catalysis selection step can be increased by decreasing the ligand concentration or the reaction time.

In one aspect, therefore, the invention features a method for obtaining a nucleic acid molecule having ligase activity. In the first step of this method, a population of candidate nucleic acid molecules, each having a region of random sequence, is contacted with a substrate nucleic acid molecule and an external template. The external template is complementary to a portion of the 3' region of the substrate nucleic acid molecule and a portion of the 5' region of each of the candidate nucleic acid molecules in the population. Alternatively, the external template may be complementary to a portion of the 5' region of the substrate nucleic acid molecule and a portion of the 3' region of each of the candidate nucleic acid molecules in the population. Binding of the external template to the substrate nucleic acid molecule and a candidate nucleic acid molecule from the population juxtaposes the 3' region of one of the molecules with the 5' region of the other.

One of the terminal nucleotides (either the 5' or the 3' nucleotide) of the juxtaposed regions may contain an activated group. Activated groups that may be used in the method of the invention include, but are not limited to, 5'-phosphoro(2-methyl)imidazolide, a 5'-phosphorimidizolide, cyanogen bromide, and carbodiimides (e.g., 1-ethyl-3-(3'-dimethylaminopropyl) carbodiimide (CDI), 1-cyclohexyl-3-(2-morpholinyl-(4)-ethyl)-carbodiimide metho-p-toluenesulfonate, CDI-1, and CDI-2). As a specific example, the activated group is a 3'-phosphorimidazolide on the 3' terminal nucleotide of the substrate. Activating groups are added to the nucleic acid molecules used in the methods of the invention by using methods known in the art.

Alternatively, if desired, this first step external templating may be omitted. It is not essential to the selection method of the invention.

In the second step of this method of the invention, a subpopulation of nucleic acid molecules having ligase activity is isolated from the population. This may be accomplished by, e.g., affinity chromatography followed by selective PCR amplification. For example, the substrate nucleic acid and/or the nucleic acid from the population may contain the first member of a specific binding pair (e.g., biotin). As a specific example, the terminal nucleotide of the substrate nucleic acid (e.g., the 5' terminal nucleotide of the substrate nucleic acid) and/or the nucleic acid molecule from the population that is not juxtaposed by the external template may be labeled with biotin. Isolation of molecules containing biotin may be accomplished by contacting the molecules with immobilized avidin, e.g., a streptavidin agarose affinity column. Other specific binding pairs known to one skilled in the art may be used in the method of the invention.

The isolated subpopulation may be amplified in vitro using, e.g., PCR. In selective PCR, the first primer is complementary to a sequence of the substrate nucleic acid molecule and the second primer is complementary to the opposite strand of a sequence in the population. Use of these primers therefore results in amplification of only those nucleic acid molecules which are a product of the ligation of the substrate to a nucleic acid molecule from the population. In order to generate a population of nucleic acid molecules for further rounds of selection, nested PCR amplification may be carried out using primers which preferably include the terminal nucleotides of the nucleic acid from the population that was ligated to the substrate nucleic acid.

The above-described steps of contacting, isolating, and amplifying may be repeated on the subpopulations of nucleic acid molecules obtained. The additional rounds of selection may be carried out in the presence or absence of the external template. Nucleic acid molecules isolated using the above-described method may be subcloned into a vector (e.g., a plasmid) and further characterized by, e.g., sequence analysis.

In a second aspect, the invention features a DNA molecule capable of acting as a catalyst. A catalyst is a molecule which enables a chemical reaction to proceed under different conditions (e.g., at a lower temperature, with lower reactant concentrations, or with increased kinetics) than otherwise possible.

In a third aspect, the invention features a DNA molecule capable of acting as a catalyst on a nucleic acid substrate. This catalysis does not require the presence of a ribonucleotide in the nucleic acid substrate.

In a fourth aspect, the invention features a nucleic acid molecule having ligase activity, e.g., DNA or RNA ligase activity. The nucleic acid molecule may be DNA, RNA, or combinations or modifications thereof.

In a fifth aspect, the invention features a nucleic acid molecule capable of ligating a first substrate nucleic acid to a second substrate nucleic acid. The rate of ligation catalyzed by the nucleic acid molecule of the invention is greater than the rate of ligation of the substrate nucleic acids by templating under the same reaction conditions which include such variables as, e.g., substrate concentration, template/enzyme concentration, nature and quantity of base-pairing interactions between substrates and template/enzyme, type of activating group, salt, pH, and temperature. Templating is the joining of two substrate nucleic acid molecules when hybridized to contiguous regions of a "template" nucleic acid strand.

In a sixth aspect, the invention features a catalytic DNA molecule capable of ligating a first substrate nucleic acid to a second substrate nucleic acid. The first substrate nucleic acid contains the sequence 3'-$S^1$-$S^2$-5', the second substrate nucleic acid contains the sequence 3'-$S^3$-$S^4$-5', and the catalytic DNA molecule contains the sequence 5'-$E^1$-TTT-$E^2$-AGA-$E^3$-$E^4$-$E^5$-$E^6$-3'.

For these substrate and catalytic DNA molecules, $S^1$ contains at least two (for example, 2–100, 4–16, or 8–12) nucleotides positioned adjacent to the 3' end of $S^2$. The $S^1$ nucleotides are complementary to an equivalent number of nucleotides in $E^1$ that are positioned adjacent to the 5' end of TTT.

$S^2$ contains one–three (for example, 1) nucleotides, $S^3$ contains one–six (for example, 3) nucleotides, and the 5' terminal nucleotide of $S^2$ and the 3' terminal nucleotide of $S^3$ alternatively contain an activated group or a hydroxyl group.

$S^4$ contains at least two (for example, 2–100, 4–16, or 8–12) nucleotides positioned adjacent to the 5' end of $S^3$. The $S^4$ nucleotides are complementary to an equivalent number of nucleotides in $E^6$ that are positioned adjacent to the 3' end of $E^5$.

$E^1$ contains at least two (for example, 2–100, 4–16, or 8–12) nucleotides positioned adjacent to the 5' end of TTT. The $E^1$ nucleotides are complementary to an equivalent number of nucleotides in $S^1$ that are positioned adjacent to the 3' end of $S^2$.

$E^2$ contains 0–12 nucleotides, for example, 3–4 nucleotides.

$E^3$ contains at least two (for example, 2–100, 3–50, 5–20, or 5) nucleotides positioned adjacent to the 3' end of said AGA, said $E^3$ nucleotides being complementary to an equivalent number of nucleotides in $E^5$ that are positioned adjacent to the 5' end of $E^6$.

$E^4$ contains at least 3 nucleotides (for example, 3–200, 3–30, 3–8, 4–6, or 5) nucleotides. Alternatively, $E^4$ may contain zero nucleotides. In this case, the 3' end of $E^3$ and the 5' end of $E^5$ would not be linked to another nucleic acid segment (e.g., $E^4$), and the enzyme therefore would be made up of two separate nucleic acid molecules (the first containing 5'-$E^1$-TTT-$E^2$-AGA-$E^3$-3', and the second containing 5'-$E^5$-$E^6$-3').

$E^5$ contains at least two (for example, 2–100, 3–50, 5–20, or 5) nucleotides positioned adjacent to the 5' end of $E^6$. The $E^5$ nucleotides are complementary to an equivalent number of nucleotides in $E^3$ that are positioned adjacent to the 3' end of AGA.

$E^6$ contains at least two (for example, 2–100, 4–16, or 8–12) nucleotides positioned adjacent to the 3' end of $E^5$. The $E^6$ nucleotides are complementary to an equivalent number of nucleotides in $S^4$ that are positioned adjacent to the 5' end of $S^3$.

In the case of long stem structures formed by, e.g., $S^1$ and $E^1$, $S^4$ and $E^6$, or $E^3$ and $E^5$, the stem structures may contain mismatches, provided that a stem structure is maintained.

The 5' most nucleotide of $S^2$, the 3' most nucleotide of $S^3$, and the second 3' most nucleotide of $S^3$ may be complementary to the 5' most nucleotide of $E^2$, the second 5' most nucleotide of $E^2$, and the third 5' most nucleotide of $E^2$, respectively. In addition, $E^2$ may contain four nucleotides, and the third 3' most nucleotide of $S^3$ may be complementary to the fourth 5' most nucleotide of $E^2$.

In a seventh aspect, the invention features a method of ligating a first nucleic acid molecule to a second nucleic acid molecule. In this method, the first and second nucleic acid molecules are contacted with a nucleic acid molecule having ligase activity (e.g., DNA ligase activity). The nucleic acid molecule having ligase activity, as well as the first and second nucleic acid molecules may contain DNA, RNA, or modifications or combinations thereof The ease with which DNA oligonucleotides can be synthesized and their relatively high stability represent major advantages over other biopolymer catalysts, such as proteins and RNA, for, e.g., industrial, research, and therapeutic applications. Other features and advantages of the invention will be apparent from the following description of the preferred embodiments thereof, and from the claims.

DETAILED DESCRIPTION

The drawings are first described.

BRIEF DESCRIPTION OF THE DRAWINGS

FIG. 2B is a schematic representation of the sequences of clones isolated from pool 9 DNA. DNA from pool 9 was amplified by PCR and cloned into pT7Blue T-Vector (Novagen, Madison, Wisc.). Each of the clones analyzed was sequenced in both directions using the standard dideoxy sequencing method. The 21 sequences (SEQ ID NOs: 1–21)

shown in the figure share a consensus sequence consisting of two conserved domains (SEQ ID NOs: 22 and 23). Upper and lower case letters in the consensus indicate highly and moderately conserved positions, respectively. X and Z represent non-conserved, but complementary bases. The bolded T in domain I is present in 50% of the clones.

Figure 3C:
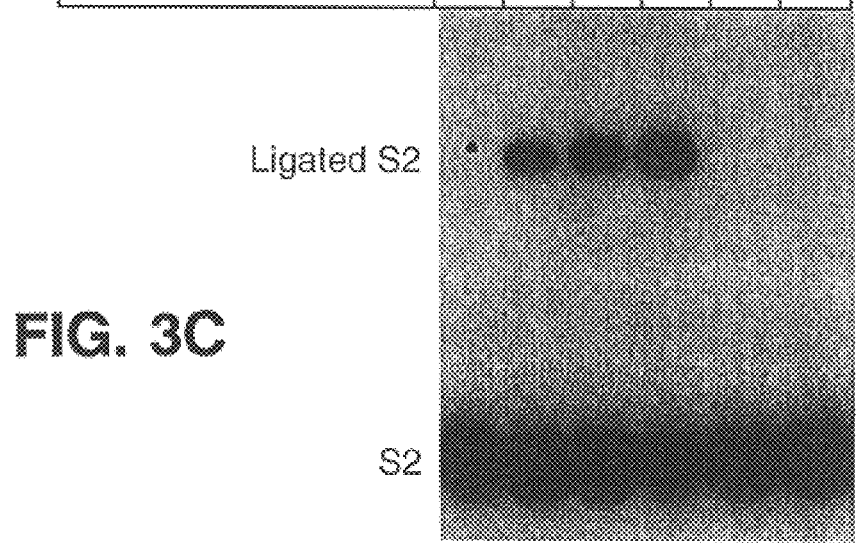
Figure 3A:
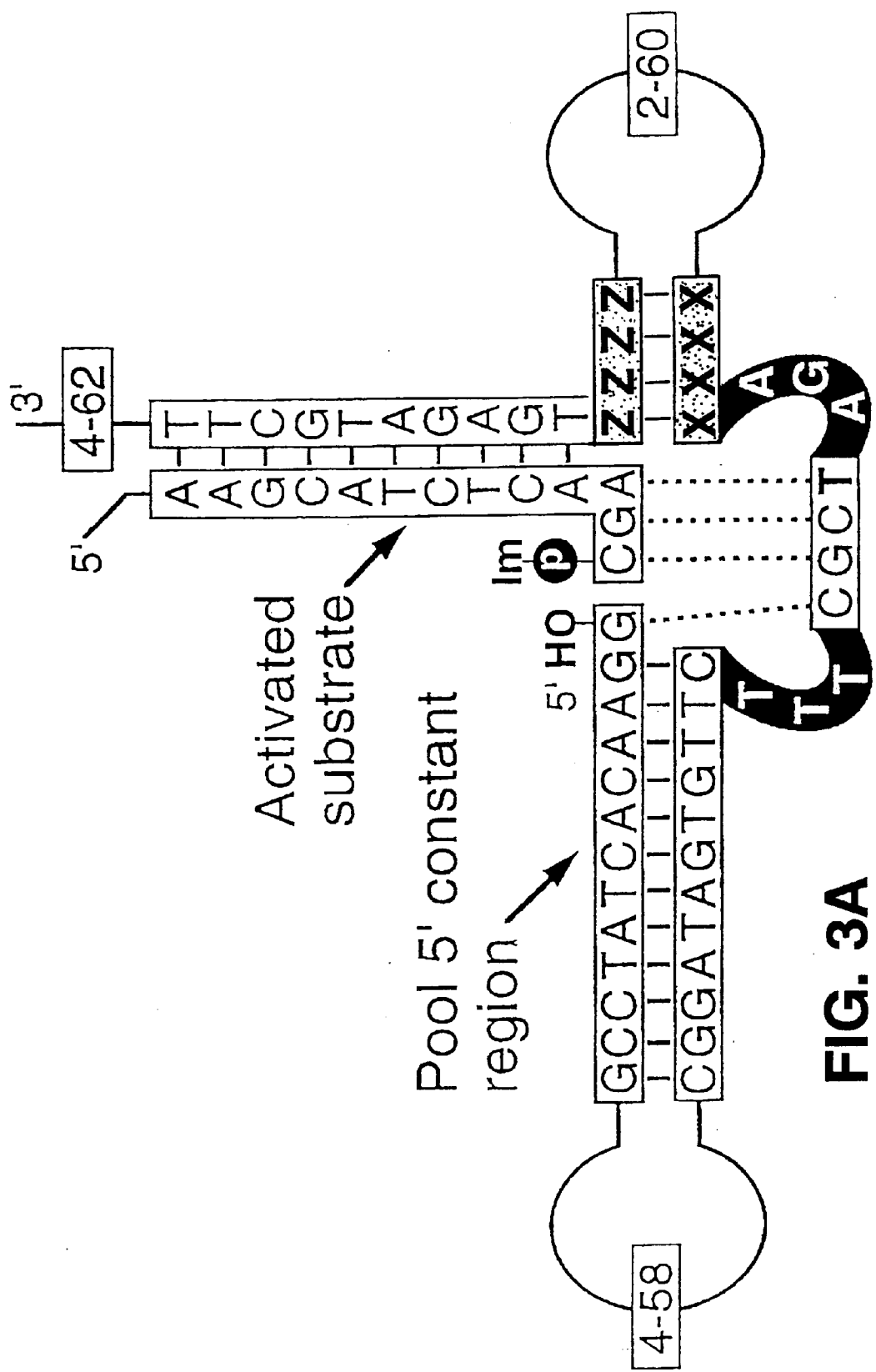

FIG. 3A is a schematic representation of the proposed secondary structure for the consensus sequence of the DNA molecules having DNA ligase activity isolated from pool 9 DNA. The 5' end of domain I and the 3' end of domain II base-pair with the 5' constant region of the pool (SEQ ID NO: 25) and the activated substrate (SEQ ID NO: 24), respectively. The two complementary regions ("NNNN" of SEQ ID NO: 26 and "NNNN" of SEQ ID NO: 27) form a stem structure and bring the flanking domains into close proximity. Dotted lines indicate possible interactions between the bases at the ligation junction and the sequence between the two boxed sequences, TTT and AGA.

Figure 3B:
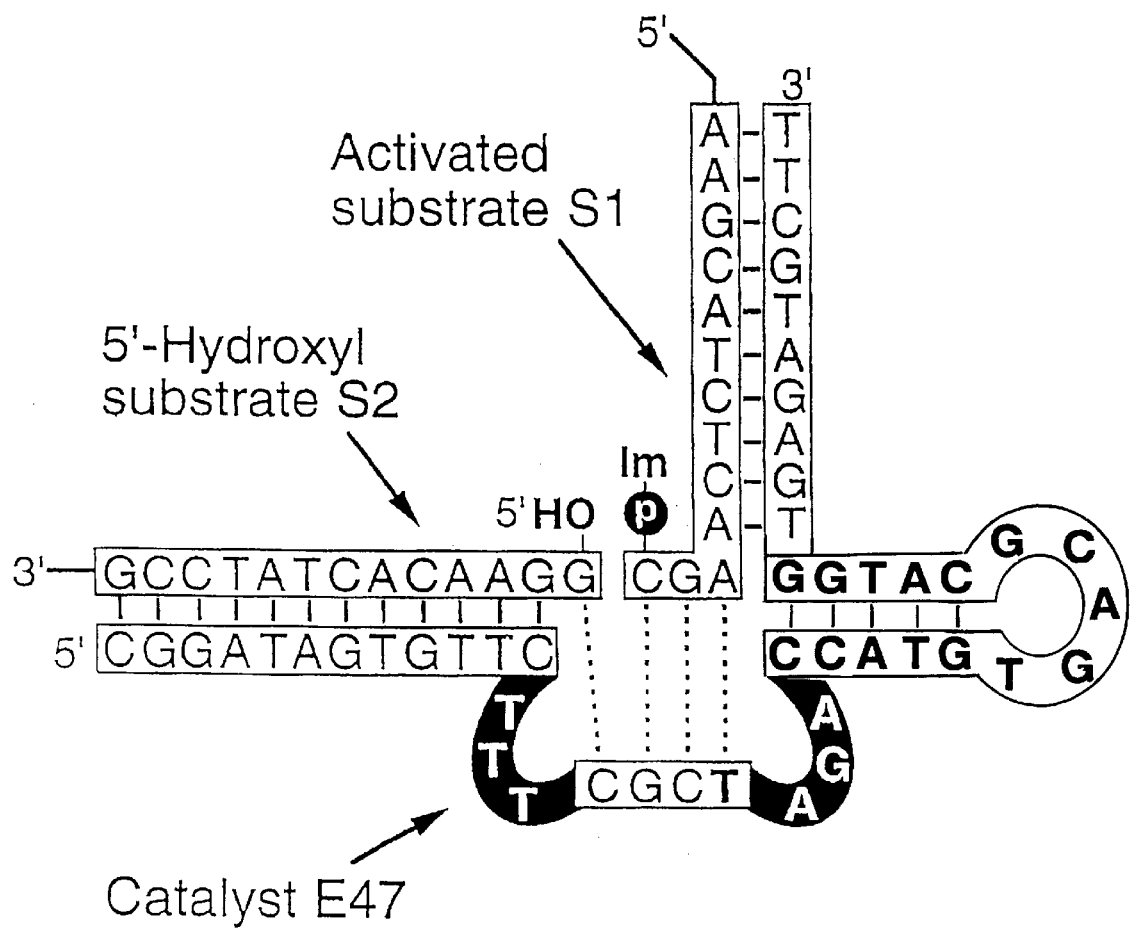

FIG. 3B is a schematic representation of a minimal DNA catalyst (SEQ ID NO: 28). Non-conserved regions in the DNA structure shown in FIG. 3A were deleted in order to generate a three-fragment complex in which the formation of a phosphodiester bond between the 3'-phosphorimidazolide substrate S1 and the 5'-hydroxyl substrate S2 is catalyzed by the 47 nucleotide metalloenzyme E47.

FIG. 3C is a denaturing acrylamide gel analysis of a time course of ligation of activated substrate S1 and radiolabeled substrate S2 by the catalyst E47. No reaction was detectable when activated S1 (lanes 1 and 5) or E47 (lane 6) was absent.

Figures 3D, 4B:
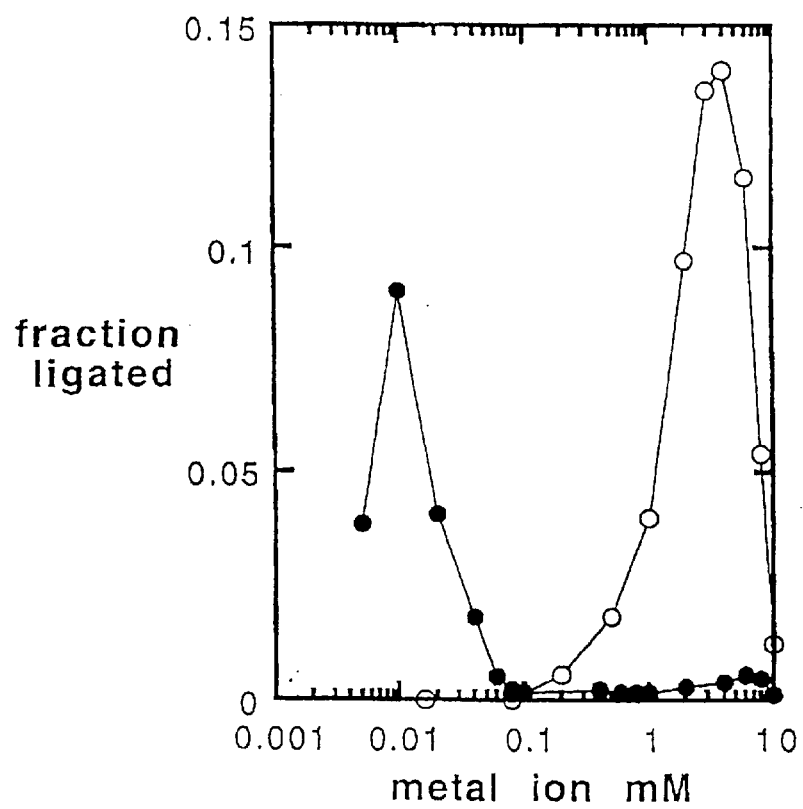

FIG. 3D is a table showing the initial rates of ligation catalyzed by E47, E47-3T, E47-AGA, E47-hairpin, and pool 9 ssDNA. Activated substrate S1 (1 $\mu$M) and radiolabeled S2 (0.5 $\mu$M; S2 was 3'-end labeled using [$\alpha$-$^{32}$P]-cordycepin-5'-triphosphate (NEN Dupont, Boston, Mass.) and terminal transferase (Promega, Madison, Wisc.)) were incubated with the different catalysts (0.75 $\mu$M) at 25° C. Reaction conditions are as in FIG. 1, with the following changes: 30 mM Hepes, pH 7.2, and 4 mM ZnCl$_2$. DNA was separated by on a 12% polyacrylamide/8 M urea gel. $K_{obs}$ values were determined by fitting fraction ligated vs. time to a linear equation using KaleidaGraph, and are the average of two independent experiments measured at less than 20% product formation. E47-3T and E47-AGA are E47 derivatives in which the conserved TTT and AGA sequences are deleted, respectively. E47-hairpin is an E47 derivative in which the hairpin has been replaced by 5'-CCATG-3'. The background reaction, containing an external template (see FIG. 1), was measured over a six hour incubation. No product was detected in the absence of the template, corresponding to a maximum rate of 2×10$^{-5}$ hr$^{-1}$.

Figure 4A:
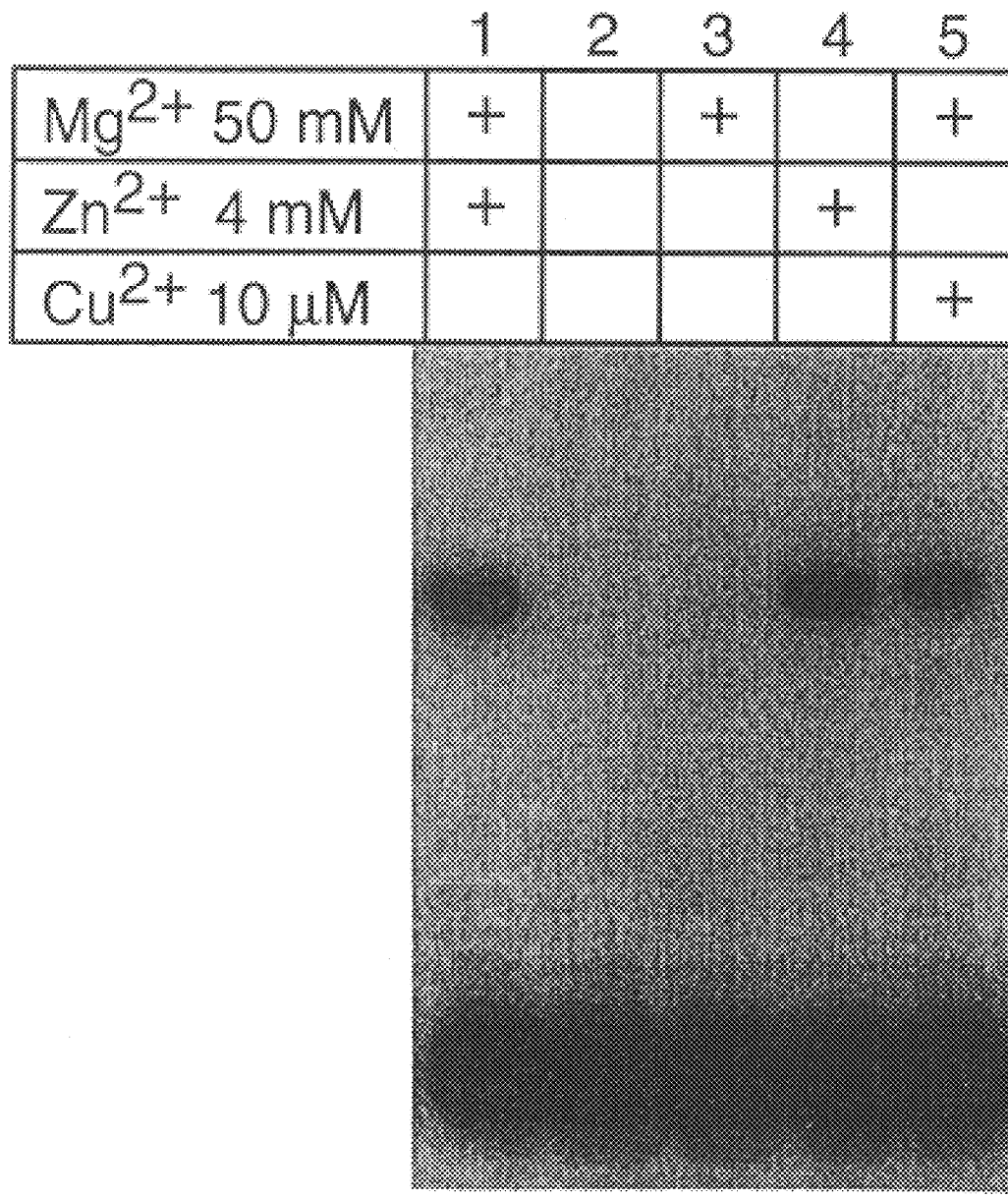

FIG. 4A is a denaturing acrylamide gel analysis of an experiment showing the effect of Mg$^{2+}$, Zn$^{2+}$, and Cu$^{2+}$ on catalysis. Reactions were incubated for 20 minutes at the indicated divalent metal ion concentrations. No reaction was detected in the absence of Zn$^{2+}$ and Mg$^{2+}$ (lane 2), or with only Mg$^{2+}$ (lane 3). Mg$^{2+}$ is not required for activity, and Zn$^{2+}$ alone (lane 4) catalyzes the reaction with the same efficiency as Zn$^{2+}$ and Mg$^{2+}$ together. Cu$^{2+}$ is the only divalent metal found that can substitute for Zn$^{2+}$ (lane 5); it does not require Mg$^{2+}$ for activity. The rate of ligation is independent of monovalent metal ions. Potassium chloride can be substituted by lithium, sodium chloride, or cesium chloride, or removed with no significant effect on product formation.

FIG. 4B is a graph showing the effects of zinc (○) and copper (●) concentrations on product formation. The reaction incubation time was 7 minutes.

Figure 4C:
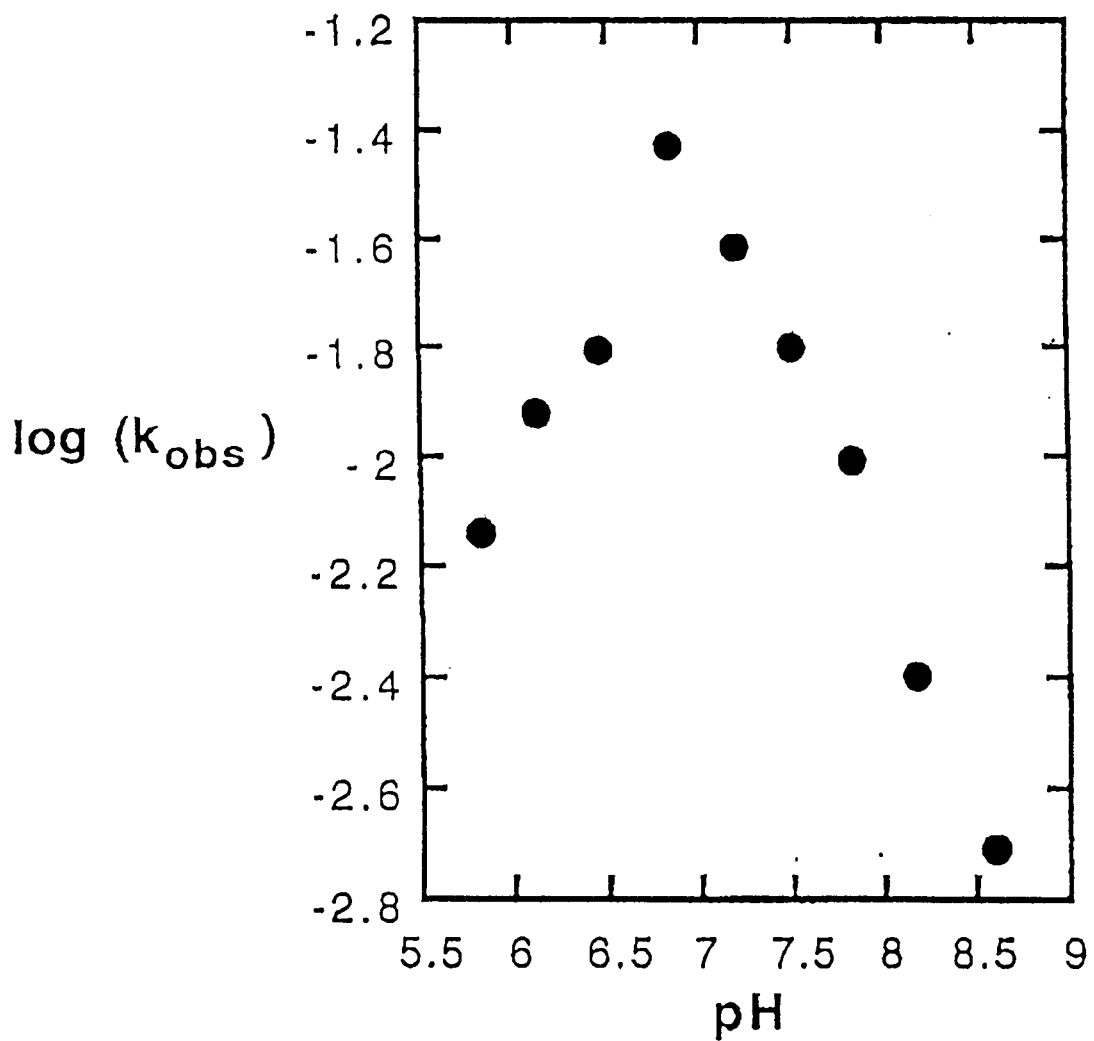

FIG. 4C is a graph showing log ($K_{obs}$) versus pH. In the presence of 10 $\mu$M CuCl$_2$, there is a linear correlation between the log of $K_{obs}$ and pH, with a slope of 0.7 up to pH 6.8. At higher pH values, the activity decreases linearly with a slope of −0.7. A slope close to +1 suggests that proton abstraction is involved in the rate determining step of the reaction, while a slope of −1 is indicative of proton donation (Fersht, *Enzyme Structure and Mechanism* (Freeman, New York, 1985)). The observed rate is independent of buffer concentration between 30–150 mM. A similar effect was observed with Zn$^{2+}$ $^{at}$ 4 mM up to pH 7.4. At higher pH, the activity drops drastically, possibly due to the formation of insoluble metal oxides or hydroxides (Bailar, Jr. et al., *Comprehensive Inorganic Chemistry* (Pergamon Press Ltd., 1973)). The reaction conditions were as specified in the description of FIG. 3.

Isolation of DNA Molecule Having DNA Ligase Activity

Figure 1:
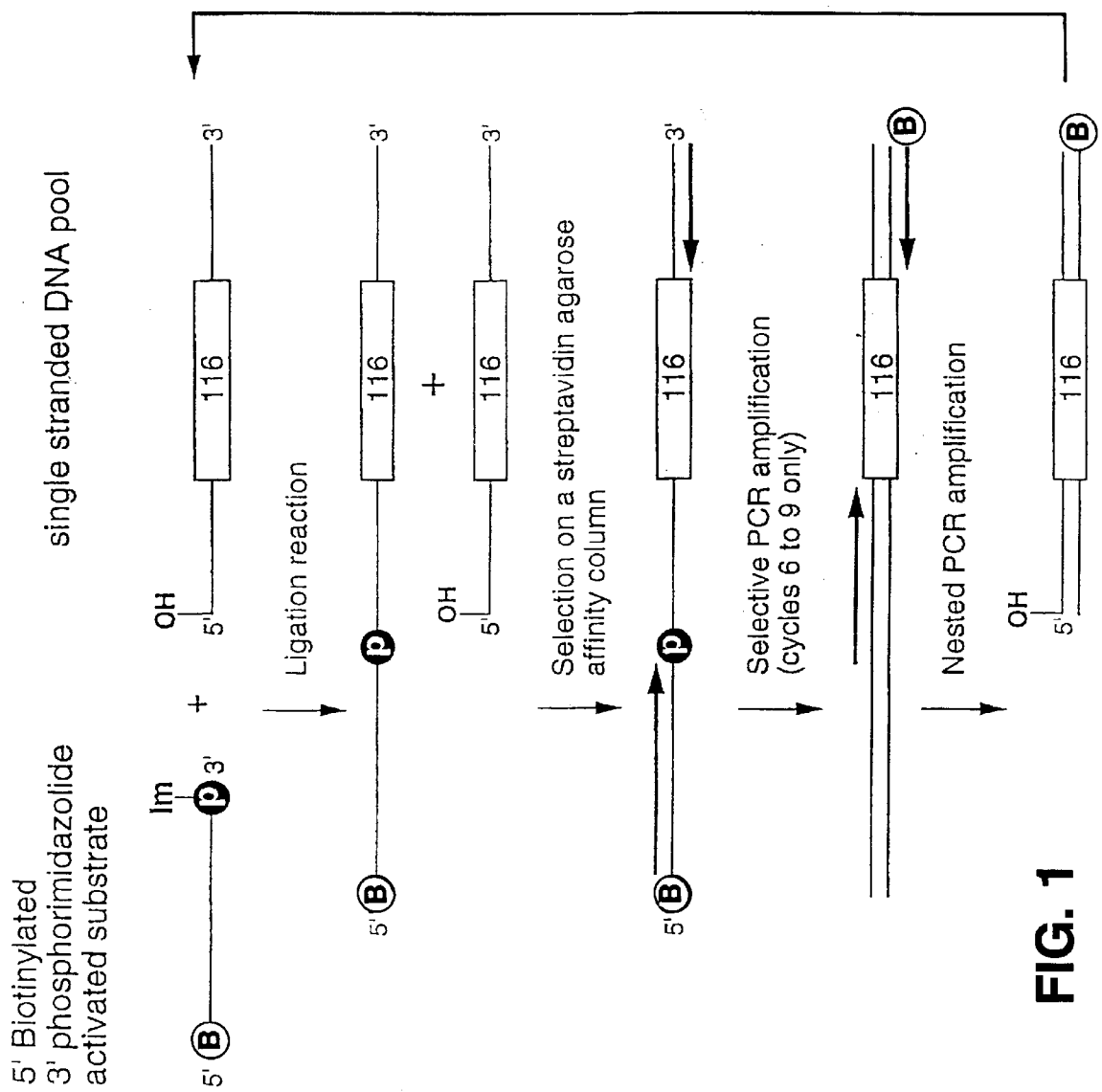
FIG. 1 is a schematic representation of the in vitro selection strategy used to isolate DNA molecules having DNA ligase activity. Each molecule in the single stranded DNA (ssDNA) pool contained 116 random bases flanked by constant regions having sequences complementary to the PCR primers 5'-GGAACACTATCCGACTGGCACC-3' (SEQ ID NO: 29) and 5'-biotin-CGGGATCCTAATGACCAAGG-3' (SEQ ID NO: 30). The pool was prepared by solid-phase phosphoramidite chemistry and amplified by PCR (Ellington et al., Nature 355:850–852, 1992) to yield approximately 32 copies of $3.5 \times 10^{14}$ different molecules. Single stranded DNA was prepared from the amplified pool as described by Bock et al. (Nature 355:564–566, 1992). The activated substrate (5'-biotin-AAGCATCTAAGCATCTCAAGC-p-Im (SEQ ID NO: 31)) contained a 5'-biotin group and a 3'-phosphorimidazolide (Chu et al., Nucleic Acids Res. 14:5591–5603, 1986). Eight copies of the DNA pool (0.5 µM) were incubated in selection buffer (30 mM Hepes, pH 7.4, 600 mM KCl, 50 mM $MgCl_2$, 1 mM $ZnCl_2$) with 1 µM activated substrate and 1 µM of an external template (5'-CGGATAGTGTTCCGCTTGAGATGCTT-3' (SEQ ID NO: 32)) complementary to the 5' end of the pool and the 3' end of the activated substrate. After a two hour incubation, the reaction was stopped by addition of EDTA. 0.5% ligated product was present after 24 hr. No product formation was observed in the absence of the external template. At cycle 7, pool activity was independent of the external template, indicating that the remaining pool molecules were using an internal substrate binding site. In cycles 8 and 9, no external template was added, and the reaction time was decreased to 2 and 0.5 minutes, respectively, in order to increase selection stringency. To isolate ligated molecules, the reacted pool was passed through a streptavidin agarose affinity column (Pierce, Rockford, Ill.), unligated pool was washed off the column under denaturing conditions (3 M urea followed by 150 mM NaOH, 40 column volumes each), and the ligated pool was specifically eluted with excess free biotin (Wilson et al., Nature, in press, 1995). To select for substrate ligation to the 5'-hydroxyl of the pool molecules, isolated DNA was selectively PCR amplified (in cycles 6–9 only) with a first primer corresponding to the substrate sequence and a second primer complementary to the 3' constant region of the pool, and gel purified. This pool was then subjected to nested PCR with the first set of primers, gel purified, and re-amplified for ssDNA isolation (Bock et al., Nature 355:564–566, 1992). Nine cycles of selection-amplification were performed, after which the pool activity remained constant.

Oligodeoxynucleotides can be non-enzymatically ligated on either single-stranded (Naylor et al., Biochemistry 5:2722–2728, 1966) or duplex (Luebke et al., J. Am. Chem. Soc. 111:8733–8735, 1989) DNA templates. We designed an in vitro selection strategy (Szostak, Trends Biochem. Sci. 17:89–93, 1992; Chapman et al., Curr. Opin. Struct. Biol. 4:618–622, 1994; Breaker et al., Trends Biotechnol. 12:268–275, 1994; Joyce, Curr. Opin. Struct. Biol. 4:331–336, 1994) in order to determine whether DNA sequences which catalyze DNA ligation more efficiently than non-enzymatic templating could be isolated from a large pool of random sequences (FIG. 1). Using this strategy, a small single-stranded DNA that is a Zn$^{2+}$/Cu$^{2+}$-dependent metalloenzyme was isolated. The enzyme catalyzes the formation of a new phosphodiester bond by the condensation of the 5'-hydroxyl group of one oligodeoxynucleotide and a 3'-phosphorimidazolide group on another oligodeoxynucleotide, and shows multiple turnover ligation.

Figure 2A:
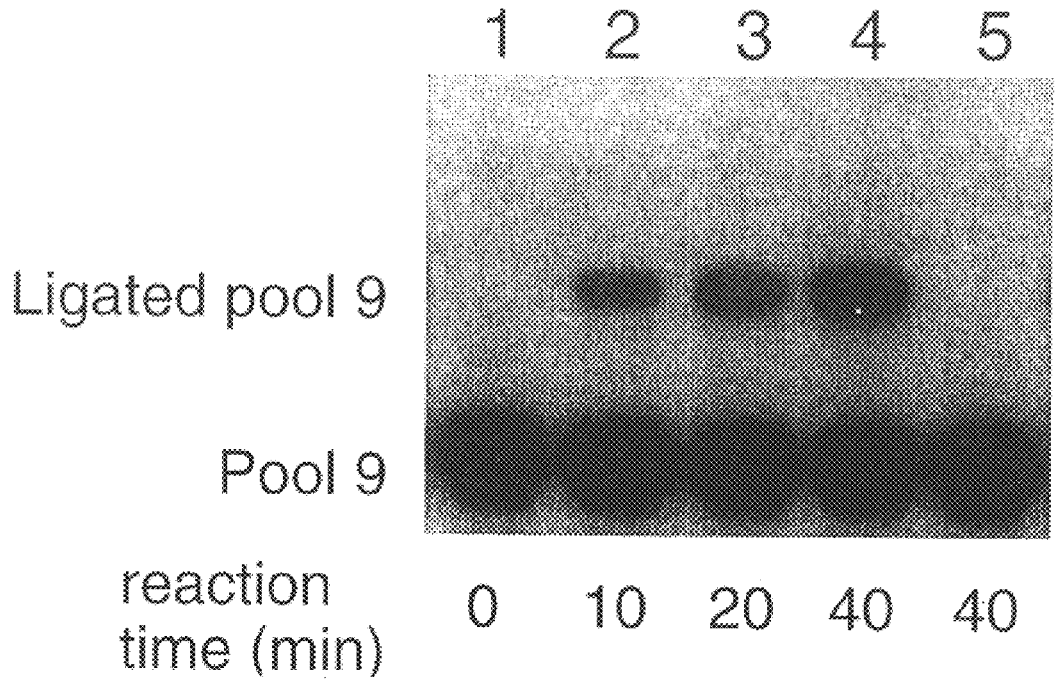
FIG. 2A is a denaturing acrylamide gel analysis of a time course of ligation reactions catalyzed by pool 9 ssDNA. Internally labeled pool 9 DNA (0.5 µM) was incubated with activated substrate (1 µM) in selection buffer for the indicated times. In a control reaction, the substrate was not activated (lane 5). DNAs were separated by electrophoresis in a 6% polyacrylamide/8 M urea gel. Radioactivity was detected using a Molecular Dynamics Phosphorimager.

The details of the selection strategy are illustrated in FIG. 1. After nine cycles of selection and amplification, the DNA pool (pool 9) displayed efficient ligation activity (FIG. 2A). Incubation of pool 9 DNA with the activated substrate yields a ligated product with the correct molecular weight and the expected nucleotide sequence at the ligation junction. To analyze further the selected sequences, DNA from pool 9 was cloned and sequenced. The majority of the clones contain a common consensus sequence consisting of two small domains separated by a spacer region of variable length and sequence (FIG. 2B). The two small domains are embedded in entirely different flanking sequences, indicating that several independent sequences in the original pool were carried through the selection process. Inspection of the consensus sequence suggests a secondary structure that is more complex than a simple template, but nevertheless brings the 5'-hydroxyl group and the 3'-phosphorimidazolide group into close proximity (FIG. 3A).

Based on the consensus sequence, a small 47 nt ssDNA catalyst (E47) was designed that ligates two separate DNA substrates, S1 and S2 (FIG. 3B). Incubation of radiolabeled S2 with activated substrate S1 and E47 catalyst results in the appearance of the expected ligated product (FIG. 3C). Product formation requires that all three components are present in the reaction. In addition, the 3'-phosphate group of S1 must be activated. E47 catalyzes the ligation reaction twice as fast as pool 9. Small deletions within E47 result in severe losses of catalytic efficiency (FIG. 3D), indicating that the central consensus sequence is necessary for catalysis. The initial rate of ligation of S1 and S2 by E47 is 3400-fold greater than the rate of the same reaction catalyzed by a simple complementary template under the same conditions, and is at least $10^5$-fold faster than the untemplated background ligation (FIG. 3D). This rate enhancement is comparable to values obtained for ribozymes obtained by in vitro selection (Szostak, Trends Biochem. Sci. 17:89–93, 1992; Chapman et al., Curr. Opin. Struct. Biol. 4:618–622, 1994; Breaker et al., Trends Biotechnol. 12:268–275, 1994; Joyce, Curr. Opin. Struct. Biol. 4:331–336, 1994) and catalytic antibodies (Lerner et al., Science 252:659–667, 1991).

Since the catalyst is not consumed in the reaction, it was expected that E47 would be capable of catalyzing the ligation of several molar equivalents of substrates S1 and S2, provided that the ligated product is able to dissociate from the enzyme. At saturating concentrations (140 $\mu$M) of both substrates and 1 $\mu$M E47, multiple turnover catalysis at a rate of 0.66 $hr^{-1}$ at 25° C. and 2.4 $hr^{-1}$ at 35° C. was observed (10 turnovers observed). At these temperatures, product release appears to be rate limiting, as a rapid initial burst of approximately one equivalent of product formation was observed within the first 10 minutes of the reaction. The initial rate of ligation in this burst phase was directly proportional to the concentration of E47 over a 30-fold range, as expected for an enzyme at saturating substrate concentration (Fersht, Enzyme Structure and Mechanism (Freeman, New York, 1985)). A plot of $K_{obs}$ vs. [E47] yielded a $k_{cat}$ of 3.2 $hr^{-1}$ (0.07 $min^{-1}$) at 25° C.

Because divalent metal ions play a crucial role in ribozymes (Pyle, Science 261:709–714, 1993) and many protein enzymes (Karlin, Science 261:701–708, 1993), it was expected that the DNA catalyst would require either $Mg^{2+}$ and/or $Zn^{2+}$ for activity, as these ions were present in the selection buffer. Indeed, the ligation reaction is dependent on $Zn^{2+}$ (FIG. 4A), but does not require $Mg^{2+}$. All of the members of the Irving-Williams series ($Ba^{2+}$, $Sr^{2+}$, $Ca^{2+}$, $Mg^{2+}$, $Mn^{2+}$, $Fe^{2+}$, $Co^{2+}$, $Ni^{2+}$, $Cu^{2+}$, $Zn^{2+}$), as well as $Pb^{2+}$ and $Cd^{2+}$, were tested at concentrations between 10 $\mu$M and 10 mM, and it was found that only $Cu^{2+}$ could substitute for $Zn^{2+}$. The efficiency of the ligation reaction is highly dependent on the divalent metal ion concentration (FIG. 4B). Increasing concentrations of $Zn^{2+}$ up to 4 mM enhanced activity, but at higher concentrations the activity dropped sharply, suggesting the existence of inhibitory metal binding sites. A similar concentration dependence was observed for copper, but at a 400-fold lower concentration. The metal ion specificity suggests the existence of one or more metal ion binding sites with stringent geometrical and/or size requirements.

To gain insight into the ligation mechanism, the pH-rate profile of the reaction under pre-steady-state (single turnover) conditions was determined (FIG. 4C). The bell shaped profile displayed with $Cu^{2+}$ suggests that the rate limiting step of the ligation reaction depends in part on two ionizable groups, once acidic and one basic, raising the possibility of a general acid-base mechanism (Fersht, Enzyme Structure and Mechanism (Freeman, New York, 1985)) in which copper complexes are involved in proton transfer. Metal-ion hydroxides are thought to act as general bases in some ribozyme-mediated RNA cleavage reactions (Pyle, Science 261:709–714, 1993; Dahm et al., Biochemistry 32:13040–13045, 1993; Pan et al., Biochemistry 33:9561–9565, 1994). Other possibilities, such as pH-dependent folding effects, may also account for these observations (Kao et al., Proc. Natl. Acad. Sci. USA 77:3360–3364, 1980).

E47 and substrates S1 and S2 were modified so that ligation of the modified substrates by the modified enzyme results in formation of a ligated product having the sequence of the modified enzyme. The sequences of three such enzymes (E), and their corresponding substrates (S1 and S2), are as follows:

I. E: 5'-ACCTTCACCTTCTTTCGCTAGACCTTCAAGC-GGAAGGTGAAGGT CTAGCG-3' (SEQ ID NO: 33)

S1:
   5'-ACCTTCACCTTCTTTCGCTAGACCTTCAAGC-3' (SEQ ID NO: 34)

S2: 5'-GGAAGGTGAAGGTCTAGCG-3' (SEQ ID NO: 35)

II. E: 5'-ACCTTCACCTTCTTTCGCTAGACCTTCAAG-CGGAAGGTGAAGGT CTA-3' (SEQ ID NO: 36)

S1:
   5'-ACCTTCACCTTCTTTCGCTAGACCTTCAAGC-3' (SEQ ID NO: 34)

S2: 5'-GGAAGGTGAAGGTCTA-3' (SEQ ID NO: 37)

III. E: 5'-CTTCACCTTCTTTCGCTAGACCTTCAAGC-GGAAGGTGAAGGT CTA-3' (SEQ ID NO: 38)

S1: 5'-CTTCACCTTCTTTCGCTAGACCTTCAAGC-3' (SEQ ID NO: 39)

S2: 5'-GGAAGGTGAAGGTCTA-3' (SEQ ID NO: 37)

The differences between these enzymes and E47 are in (1) the stem formed between E47 and the 5'-hydroxyl-containing substrate S2, (2) the stem formed between E47 and the activated substrate S1, (3) the intramolecular stem in E47, and (4) the loop in E47. The sequence of the presumed core of the ligation site was not changed. The modified enzymes differ from one another only in the number of base pairs between the enzyme and the substrates. The modified enzymes catalyze ligation of their respective substrates, which shows that the primary nucleotide sequences of at least some parts of the stem and loop structures depicted in FIG. 3B are not required for enzyme activity, and further that the unchanged regions of the enzyme are sufficient for maintenance of ligase activity, in the presence of the stem structures defined by $S^1$-$E^1$ and $S^4$-$E^6$.

What is claimed is:

1. A method for obtaining a nucleic acid molecule having ligase activity, said method comprising the steps of:
   a) providing a population of candidate nucleic acid molecules, each having a region of random sequence;
   b) contacting said population with:
      (i) a substrate nucleic acid molecule; and
      (ii) an external template complementary to a portion of the 3' region of said substrate nucleic acid molecule and a portion of the 5' region of each of the candidate nucleic acid molecules in said population, wherein binding of said external template to said substrate nucleic acid molecule and a candidate nucleic acid molecule from said population juxtaposes said 3' and 5' regions, and the terminal nucleotide of either said 3' or said 5' region contains an activated group;
   c) isolating a subpopulation of nucleic acid molecules having ligase activity from said population;
   d) amplifying said subpopulation in vitro;
   e) optionally repeating steps b–d for said amplified subpopulation; and
   f) isolating said nucleic acid molecule having ligase activity from said amplified subpopulation.

2. The method of claim 1, wherein said optional repeating of steps b–d is carried out in the absence of said external template.

3. The method of claim 1, wherein said nucleic acid molecule having ligase activity is DNA.

4. The method of claim 1, wherein said substrate nucleic acid molecule is DNA.

5. The method of claim 1, wherein the 5' terminal nucleotide of said substrate nucleic acid contains a biotin moiety.

6. The method of claim 1, wherein said activated group is a 3'-phosphorimidazolide on the 3' terminal nucleotide of said substrate.

7. A catalytic DNA molecule capable of ligating a first substrate nucleic acid to a second substrate nucleic acid, said first substrate nucleic acid comprising the sequence 3'-$S^1$-$S^2$-5', said second substrate nucleic acid comprising the sequence 3'$S^3$-$S^4$-5', and said catalytic DNA molecule comprising the sequence 5'-$E^1$-TTT-$E^2$-AGA-$E^3$-$E^4$-$E^5$-$E^6$-3', wherein $S^1$ comprises at least two nucleotides positioned adjacent to the 3' end of $S^2$, said $S^1$ nucleotides being complementary to an equivalent number of nucleotides in $E^1$ that are positioned adjacent to the 5' end of said TTT;

$S^2$ comprises one–three nucleotides, $S^3$ comprises one–six nucleotides, and the 5' terminal nucleotide of $S^2$ and the 3' terminal nucleotide of $S^3$ alternatively contain an activated group or a hydroxyl group;

$S^4$ comprises at least two nucleotides positioned adjacent to the 5' end of $S^3$, said $S^4$ nucleotides being complementary to an equivalent number of nucleotides in $E^6$ that are positioned adjacent to the 3' end of $E^5$;

$E^1$ comprises at least two nucleotides positioned adjacent to the 5' end of said TTT, said $E^1$ nucleotides being complementary to an equivalent number of nucleotides in $S^1$ that are positioned adjacent to the 3' end of $S^2$;

$E^2$ comprises zero–twelve nucleotides;

$E^3$ comprises at least two nucleotides positioned adjacent to the 3' end of said AGA, said $E^3$ nucleotides being complementary to an equivalent number of nucleotides in $E^5$ that are positioned adjacent to the 5' end of $E^6$;

$E^4$ comprises 3–200 nucleotides;

$E^5$ comprises at least two nucleotides positioned adjacent to the 5' end of $E^6$, said $E^5$ nucleotides being complementary to an equivalent number of nucleotides in $E^3$ that are positioned adjacent to the 3' end of said AGA; and $E^6$ comprises at least two nucleotides positioned adjacent to the 3' end of $E^5$, said $E^6$ nucleotides being complementary to an equivalent number of nucleotides in $S^4$ that are positioned adjacent to the 5' end of $S^3$.

8. The catalytic DNA molecule of claim 7, wherein $E^2$ comprises three–four nucleotides.

9. The catalytic DNA molecule of claim 8, wherein the 5' most nucleotide of $S^2$ is complementary to the 5' most nucleotide of $E^2$; the 3' most nucleotide of $S^3$ is complementary to the second 5' most nucleotide of $E^2$; and the second 3' most nucleotide of $S^3$ is complementary to the third 5' most nucleotide of $E^2$.

10. The catalytic DNA molecule of claim 9, wherein $E^2$ comprises four nucleotides, and the third 3' most nucleotide of $S^3$ is complementary to the fourth 5' most nucleotide of $E^2$.

11. The catalytic DNA molecule of claim 7, wherein $S^2$ comprises one nucleotide.

12. The catalytic DNA molecule of claim 7, wherein $S^3$ comprises three nucleotides.

13. The catalytic DNA molecule of claim 7, wherein $E^4$ comprises five nucleotides.

14. The catalytic DNA molecule of claim 7, wherein $E^5$ and $E^3$ each comprise five nucleotides.

15. A DNA molecule having ligase activity obtained by the steps of:

(a) providing a population of candidate DNA molecules, each having a region of random sequence;

(b) contacting said population with
  (i) a substrate nucleic acid molecule; and
  (ii) an external template complementary to a portion of the 3' region of said substrate nucleic acid molecule and a portion of the 5' region of each of the candidate nucleic acid molecules in said population, wherein binding of said external template to said substrate nucleic acid molecule and a candidate nucleic acid molecule from said population juxtaposes said 3' and 5' regions, and the terminal nucleotide of either said 3' or said 5' region contains an activated group;

(c) isolating a subpopulation of DNA molecules having ligase activity from said population;

(d) amplifying said subpopulation in vitro;

(e) optionally repeating steps b–d for said amplified subpopulation; and (f) isolating said DNA molecule having ligase activity from said amplified subpopulation.

16. The DNA molecule having ligase activity of claim 15, wherein the 5' terminal nucleotide of said substrate nucleic acid contains a biotin moiety.

17. The DNA molecule having ligase activity of claim 15, wherein said activated group is a 3'-phosphorimidazolide on the 3' terminal nucleotide of said substrate.

* * * * *

UNITED STATES PATENT AND TRADEMARK OFFICE
CERTIFICATE OF CORRECTION

PATENT NO.   : 5,910,408
DATED        : June 8, 1999
INVENTOR(S)  : Jack W. Szostak et al.

It is certified that error appears in the above-identified patent and that said Letters Patent is hereby corrected as shown below:

Column 8,
Line 2, replace the black blur with -- ● --;
Line 14, replace "$ZN^{2+\ at}$" with -- $Zn^{2+}$ at --; and Column 27,
Line 17, replace "$3'S^3$" with -- $3'-S^3$ --.

Signed and Sealed this

Seventh Day of October, 2003

JAMES E. ROGAN
*Director of the United States Patent and Trademark Office*